(12) United States Patent
Scheller

(10) Patent No.: US 9,415,156 B2
(45) Date of Patent: *Aug. 16, 2016

(54) MULTI-UTILITY SURGICAL INSTRUMENT

(71) Applicant: Gregg D Scheller, Wildwood, MO (US)

(72) Inventor: Gregg D Scheller, Wildwood, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,308

(22) Filed: Jul. 30, 2014

(65) Prior Publication Data

US 2014/0343528 A1    Nov. 20, 2014

Related U.S. Application Data

(63) Continuation of application No. 13/602,016, filed on Aug. 31, 2012, now Pat. No. 8,821,444.

(51) Int. Cl.
| | |
|---|---|
| *A61M 5/178* | (2006.01) |
| *A61M 5/14* | (2006.01) |
| *A61B 1/018* | (2006.01) |
| *A61B 17/30* | (2006.01) |
| *A61B 17/00* | (2006.01) |
| *A61M 5/31* | (2006.01) |
| *A61B 17/29* | (2006.01) |

(52) U.S. Cl.
CPC .................. *A61M 5/14* (2013.01); *A61B 1/018* (2013.01); *A61B 17/00234* (2013.01); *A61B 17/30* (2013.01); *A61B 90/70* (2016.02); *A61M 5/31* (2013.01); *A61B 17/29* (2013.01); *A61B 2017/00292* (2013.01); *A61B 2017/305* (2013.01); *A61B 2217/005* (2013.01); *A61B 2217/007* (2013.01); *A61M 2005/1403* (2013.01)

(58) Field of Classification Search
CPC ..................... A61B 1/018; A61B 2017/00292; A61B 2017/305
See application file for complete search history.

(56) References Cited

U.S. PATENT DOCUMENTS

| | | | |
|---|---|---|---|
| 5,355,871 A | 10/1994 | Hurley et al. | |
| 5,893,873 A * | 4/1999 | Rader | A61B 17/2909 606/205 |
| 6,488,695 B1 | 12/2002 | Hickingbotham | |
| 6,730,076 B2 | 5/2004 | Hickingbotham | |
| 6,863,668 B2 | 3/2005 | Gillespie et al. | |
| 7,632,242 B2 | 12/2009 | Griffin et al. | |
| 7,766,904 B2 | 8/2010 | Mc Gowan, Sr. et al. | |
| 8,038,692 B2 | 10/2011 | Valencia et al. | |
| 8,197,468 B2 | 6/2012 | Scheller et al. | |
| 8,821,444 B2 * | 9/2014 | Scheller | A61B 17/30 604/164.02 |
| 2003/0171762 A1 | 9/2003 | Forchette et al. | |
| 2007/0185514 A1 * | 8/2007 | Kirchhevel | A61F 9/00763 606/171 |

* cited by examiner

*Primary Examiner* — Kevin C Sirmons
*Assistant Examiner* — Deanna K Hall
(74) *Attorney, Agent, or Firm* — Kevin P. Rollins

(57) ABSTRACT

A multi-utility surgical instrument may include a nosecone, a handle, a housing sleeve, an actuation facilitating sleeve, a piston tube, a hypodermic tube, and an end plug. The hypodermic tube may be disposed within the piston tube; the piston tube may be disposed within the actuation facilitating sleeve; the actuation facilitating sleeve may be disposed within the housing sleeve; the end plug may be disposed within a portion of the housing sleeve; the housing sleeve and the end plug may be disposed within the handle; the nose cone may be fixed to a distal end of the handle; and the hypodermic tube may be fixed to the nosecone.

20 Claims, 9 Drawing Sheets

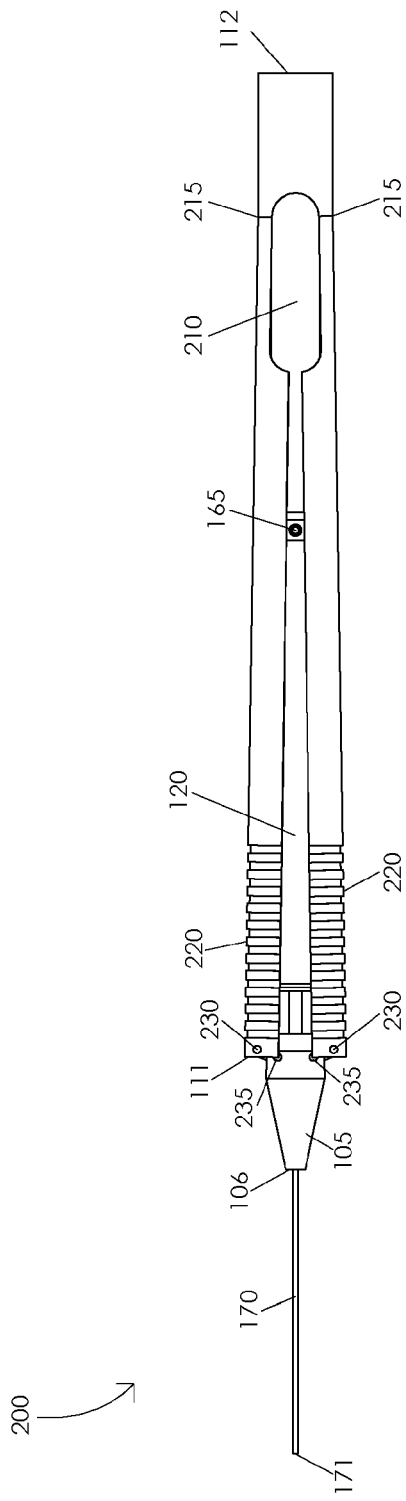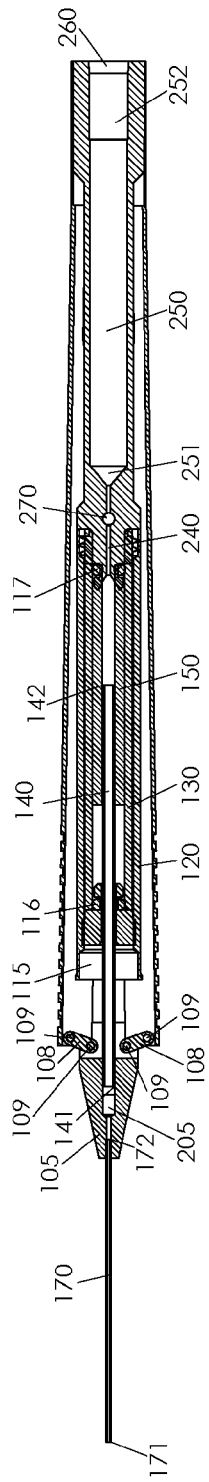
FIG. 2A
FIG. 2B

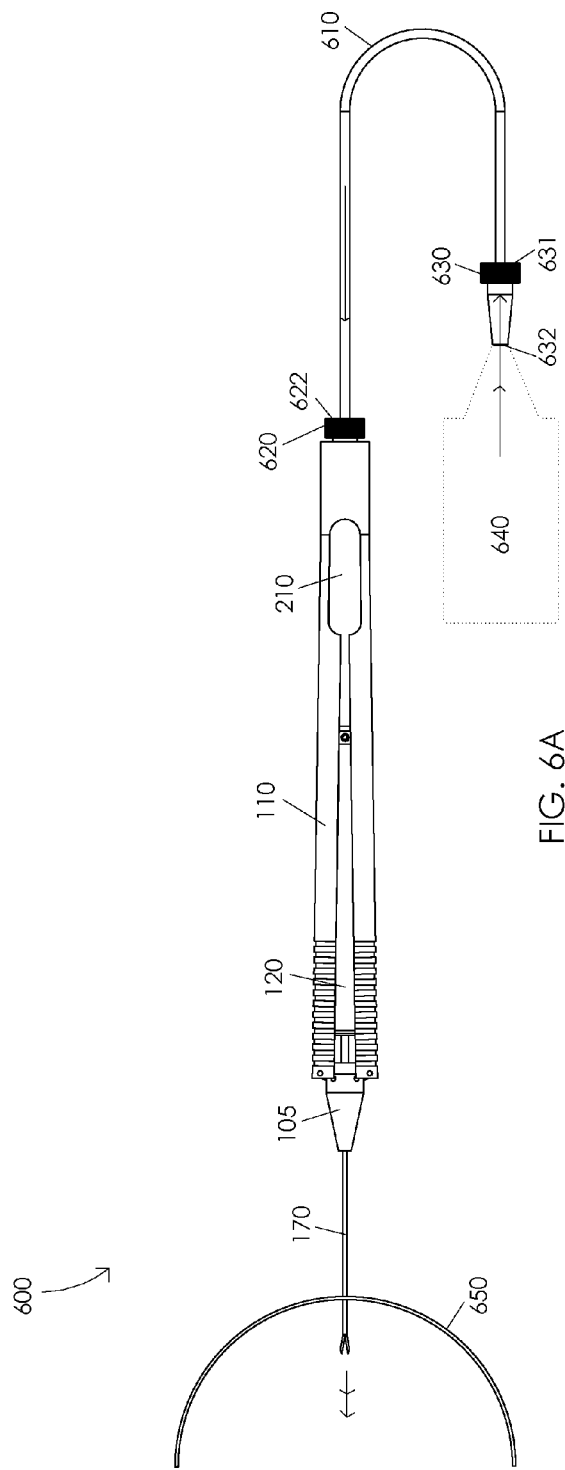
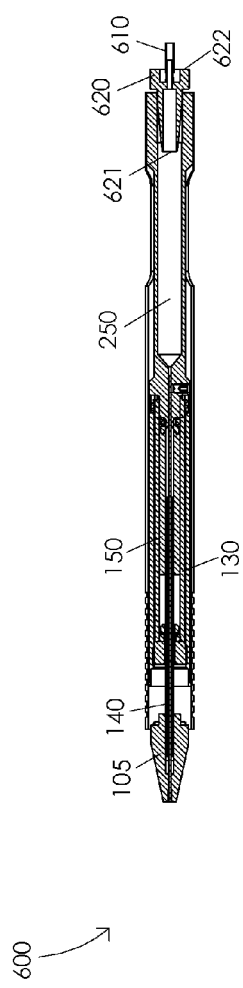
FIG. 6A
FIG. 6B

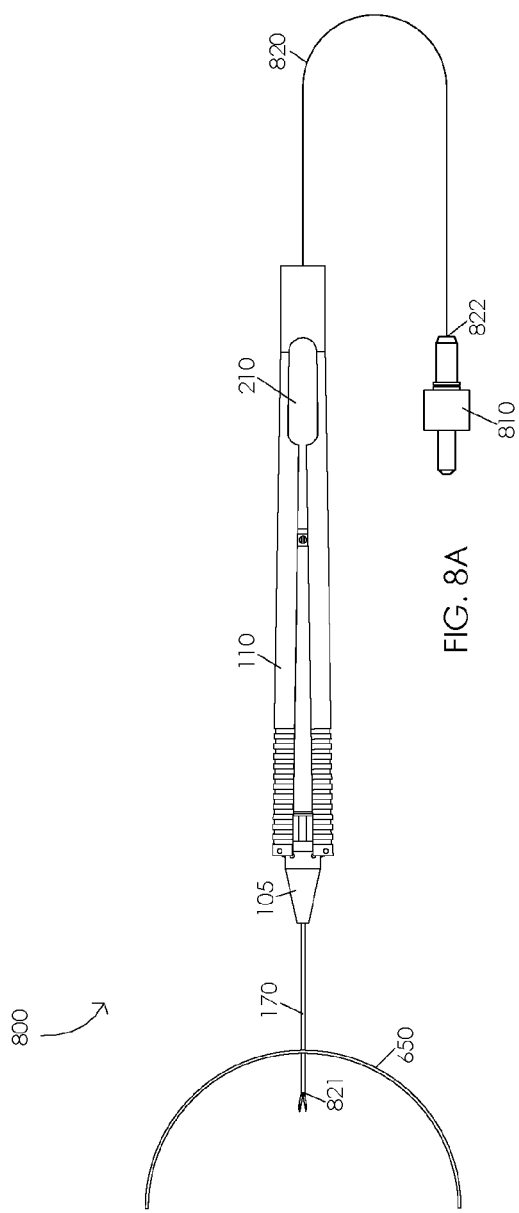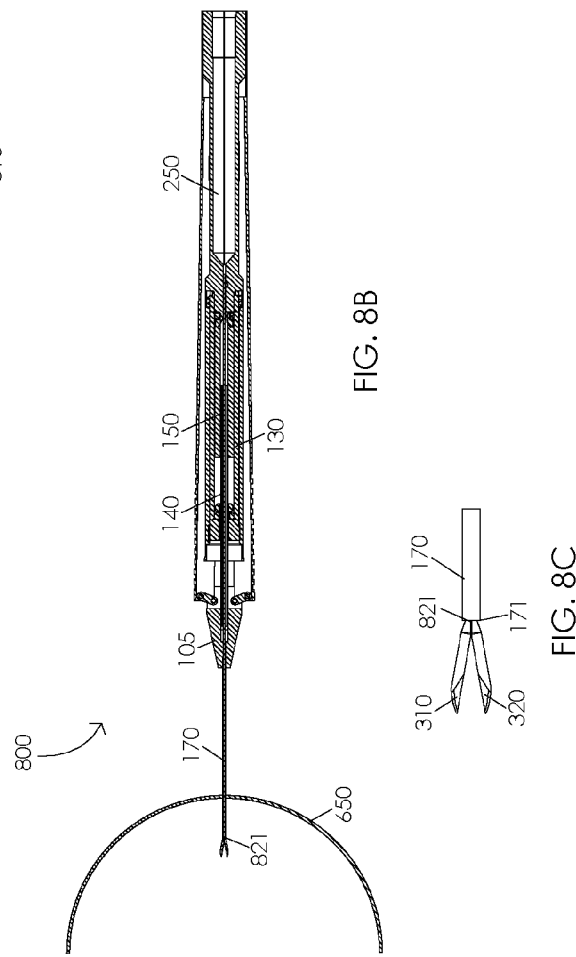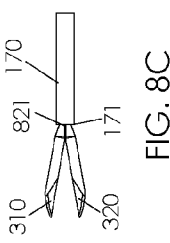

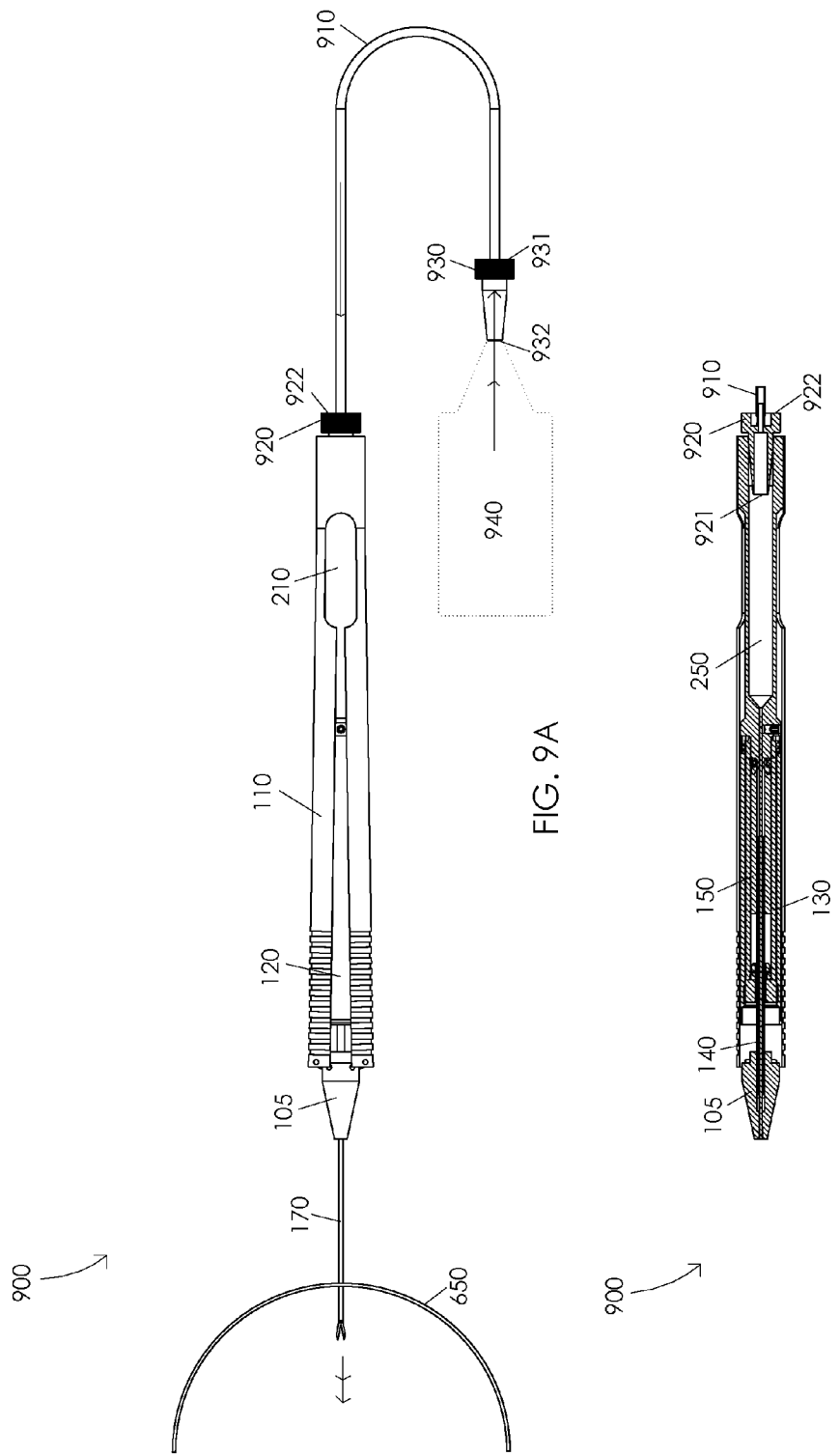

MULTI-UTILITY SURGICAL INSTRUMENT

CROSS-REFERENCE TO RELATED APPLICATIONS

This application is a continuation of prior application Ser. No. 13/602,016, filed Aug. 31, 2012, now issued as U.S. Pat. No. 8,821,444.

FIELD OF THE INVENTION

The present disclosure relates to a surgical instrument, and, more particularly, to a multi-utility surgical instrument.

BACKGROUND OF THE INVENTION

A variety of surgical procedures are performed through a very small surgical incision in a particular tissue. Reducing the size of a surgical incision during a surgical procedure generally reduces the amount of trauma to the surgical site and generally facilitates faster wound healing. In order to perform surgical procedures through a very small surgical incision, a surgeon may require specialized surgical instruments configured to fit through the very small surgical incision and provide the surgeon with a surgical utility. For example, a surgeon may perform a particular surgical procedure by inserting a first specialized surgical instrument having a first surgical utility into a very small surgical incision, and then performing a first portion of the particular surgical procedure. After performing the first portion of the particular surgical procedure, the surgeon may be required to withdraw the first specialized surgical instrument from the very small surgical incision and insert a second specialized surgical instrument having a second surgical utility into the very small surgical incision, e.g., in order to perform a second portion of the particular surgical procedure.

It is generally desirable to reduce the number of specialized surgical instruments required to perform a particular surgical procedure through a very small surgical incision. For example, every time a new surgical instrument is inserted into the very small surgical incision, there is a risk of additional trauma to the surgical site. Accordingly, there is a need for a surgical instrument configured to provide a plurality of utilities through a very small surgical incision.

BRIEF SUMMARY OF THE INVENTION

The present disclosure provides a multi-utility surgical instrument. In one or more embodiments, a multi-utility surgical instrument may comprise a nosecone, a handle, a housing sleeve, an actuation facilitating sleeve, a piston tube, a hypodermic tube, and an end plug. Illustratively, the hypodermic tube may be disposed within the piston tube; the piston tube may be disposed within the actuation facilitating sleeve; the actuation facilitating sleeve may be disposed within the housing sleeve; the end plug may be disposed within a portion of the housing sleeve; the housing sleeve and the end plug may be disposed within the handle; the nose cone may be fixed to a distal end of the handle; and the hypodermic tube may be fixed to the nosecone.

In one or more embodiments, a compression of the handle may be configured to actuate the nosecone relative to the handle wherein the nosecone is gradually extended relative to a proximal end of the handle. Illustratively, an extension of the nosecone relative to the proximal end of the handle may be configured to provide one or more surgical utilities, e.g., a closing of a forceps. In one or more embodiments, a decompression of the handle may be configured to actuate the nosecone relative to the handle wherein the nosecone is gradually retracted relative to the proximal end of the handle. Illustratively, a refraction of the nosecone relative to the proximal end of the handle may be configured to provide one or more surgical utilities, e.g., an opening of a forceps.

In one or more embodiments, a multi-utility surgical instrument may be configured to interface with one or more components, e.g., to provide one or more surgical utilities. Illustratively, an end plug of a multi-utility surgical instrument may comprise an interface taper. In one or more embodiments, the interface taper may be configured to interface with a syringe, e.g., to provide cleaning utility. For example, the syringe may be configured to flush a fluid through a multi-utility surgical instrument, e.g., to clean an inner portion of the multi-utility surgical instrument. Illustratively, the interface taper may be configured to interface with an irrigation component, e.g., to provide an irrigation utility. In one or more embodiments, the interface taper may be configured to interface with an aspiration component, e.g., to provide an aspiration utility. Illustratively, the interface taper may be configured to interface with a drug delivery component, e.g., to provide a drug delivery utility. In one or more embodiments, the interface taper may be configured to interface with an illumination component, e.g., to provide an illumination utility.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A and 2B are schematic diagrams illustrating an assembled multi-utility surgical instrument;

FIGS. 6A and 6B are schematic diagrams illustrating a multi-utility surgical instrument with an irrigation utility;

FIGS. 8A, 8B, and 8C are schematic diagrams illustrating a multi-utility surgical instrument with an illumination utility;

FIGS. 9A and 9B are schematic diagrams illustrating a multi-utility surgical instrument with a drug delivery utility.

DETAILED DESCRIPTION OF AN ILLUSTRATIVE EMBODIMENT

Figure 1:
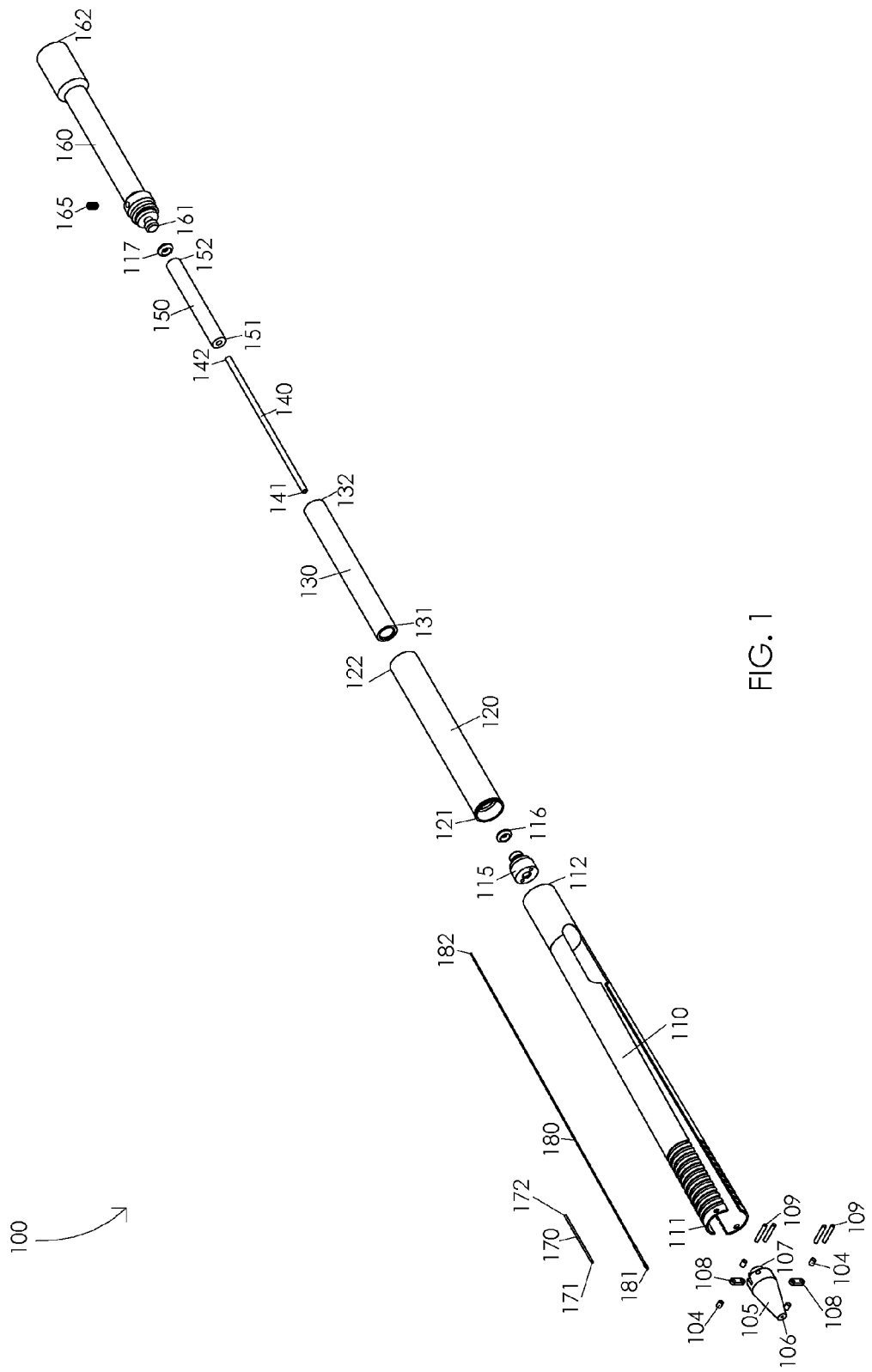
FIG. 1 is a schematic diagram illustrating an exploded view of a multi-utility surgical instrument assembly.

FIG. 1 is a schematic diagram illustrating an exploded view of a multi-utility surgical instrument assembly 100. In one or more embodiments, multi-utility surgical instrument assembly 100 may comprise a nosecone 105 having a nosecone distal end 106 and a nosecone proximal end 107; one or more links 108; one or more link pins 109; one or more spacers 104; a handle 110 having a handle distal end 111 and a handle proximal end 112; a front plug 115; a distal O-ring 116; a proximal O-ring 117; a housing sleeve 120 having a housing sleeve distal end 121 and a housing sleeve proximal end 122; an actuation facilitating sleeve 130 having an actuation facilitating sleeve distal end 131 and an actuation facilitating sleeve proximal end 132; an inner hypodermic tube 140 having an inner hypodermic tube distal end 141 and an inner hypodermic tube proximal end 142; a piston tube 150 having a piston tube distal end 151 and a piston tube proximal end 152; an end plug 160 having an end plug distal end 161 and an end plug proximal end 162; a fixation mechanism 165; an outer hypodermic tube 170 having an outer hypodermic tube distal end 171 and an outer hypodermic tube proximal end 172; and a surgical blank 180 having a surgical blank distal end 181 and a surgical blank proximal end 182.

Illustratively, outer hypodermic tube 170 may be fixed to nosecone 105, e.g., outer hypodermic tube proximal end 172 may be fixed to nosecone distal end 106. In one or more embodiments, one or more links 108 and one or more link pins 109 may be configured to connect nosecone 105 and handle 110, e.g., a portion of nosecone 105 may be disposed within handle 110. Illustratively, nosecone 105 may be connected to one or more links 108, e.g., one or more link pins 109 may be disposed within both nosecone 105 and one or more links 108. In one or more embodiments, handle 110 may be connected to one or more links 108, e.g., one or more link pins 109 may be disposed within both handle 110 and one or more links 108. Illustratively, at least one link 108 may be connected to both nosecone 105 and handle 110, e.g., by one or more link pins 109.

In one or more embodiments, inner hypodermic tube 140 may be at least partially disposed within piston tube 150, e.g., inner hypodermic tube proximal end 142 may be disposed within piston tube 150. Illustratively, inner hypodermic tube 140 and piston tube 150 may be at least partially disposed within actuation facilitating sleeve 130. In one or more embodiments, actuation facilitating sleeve 130 and piston tube 150 may be disposed within housing sleeve 120. Illustratively, inner hypodermic tube 140 may be at least partially disposed within housing sleeve 120, e.g., inner hypodermic tube distal end 141 may extend a distance from housing sleeve distal end 121.

In one or more embodiments, distal O-ring 116 may be disposed over a portion of front plug 115. Illustratively, distal O-ring 116 may be disposed within housing sleeve 120 and actuation facilitating sleeve 130. In one or more embodiments, at least a portion of front plug 115 may be disposed within housing sleeve 120 and actuation facilitating sleeve 130, e.g., housing sleeve distal end 121 and actuation facilitating sleeve distal end 131 may be disposed over a portion of front plug 115. Illustratively, proximal O-ring 117 may be disposed over a portion of end plug 160. In one or more embodiments, proximal O-ring 117 may be disposed within housing sleeve 120 and actuation facilitating sleeve 130. Illustratively, at least a portion of end plug 160 may be disposed within housing sleeve 120 and actuation facilitating sleeve 130, e.g., housing sleeve proximal end 122 and actuation facilitating sleeve proximal end 132 may be disposed over a portion of end plug 160.

In one or more embodiments, front plug 115, distal O-ring 116, housing sleeve 120, actuation facilitating sleeve 130, piston tube 150, inner hypodermic tube 140, proximal O-ring 117, and end plug 160 may be disposed within handle 110. For example, end plug 160 may be disposed within handle 110 wherein end plug proximal end 162 may be adjacent to handle proximal end 112. Illustratively, inner hypodermic tube 140 may be fixed to nosecone 105, e.g., inner hypodermic tube distal end 141 may be fixed to nosecone proximal end 107.

In one or more embodiments, surgical blank 180 may be disposed within outer hypodermic tube 170, nosecone 105, inner hypodermic tube 140, piston tube 150, and end plug 160. Illustratively, fixation mechanism 165 may be configured to fix surgical blank 180 in a position relative to handle 110. For example, fixation mechanism 165 may comprise a setscrew configured to fix surgical blank 180 in a position relative to handle 110. In one or more embodiments, fixation mechanism 165 may comprise an adhesive material configured to fix surgical blank 180 in a position relative to handle 110. Illustratively, fixation mechanism 165 may comprise any suitable means of fixing surgical blank 180 in a position relative to handle 110.

FIGS. 2A and 2B are schematic diagrams illustrating an assembled multi-utility surgical instrument 200. FIG. 2A illustrates a side view of an assembled multi-utility surgical instrument 200. In one or more embodiments, housing sleeve 120 may be disposed within handle 110. Illustratively, actuation facilitating sleeve 130 may be disposed within housing sleeve 120. In one or more embodiments, piston tube 150 may be disposed within actuation facilitating sleeve 130. Illustratively, a portion of inner hypodermic tube 140 may be disposed within piston tube 150, e.g., inner hypodermic tube proximal end 142 may be disposed within piston tube 150. In one or more embodiments, a portion of inner hypodermic tube 140 may be fixed to an inner portion of piston tube 150, e.g., by a biocompatible adhesive. For example, an actuation of inner hypodermic tube 140 relative to handle 110 may be configured to actuate piston tube 150 relative to handle 110 and an actuation of piston tube 150 relative to handle 110 may be configured to actuate inner hypodermic tube 140 relative to handle 110.

Illustratively, handle 110 may comprise a spring return aperture 210. In one or more embodiments, spring return aperture 210 may comprise one or more hinges 215. Illustratively, spring return aperture 210 may be configured to separate a first portion of handle 110 and a second portion of handle 110. In one or more embodiments, spring return aperture 210 may be configured to separate a particular point on the first portion of handle 110 from a particular point on the second portion of handle 110 at a first distance. Illustratively, an application of a compressive force to a portion of handle 110 may be configured to separate the particular point on the first portion of handle 110 from the particular point on the second portion of handle 110 at a second distance. In one or more embodiments, the first distance may be greater than the second distance.

Illustratively, handle 110 may comprise one or more surgical grip points 220. In one or more embodiments, one or more surgical grip points 220 may be configured to prevent undesirable movements of handle 110, e.g., during a surgical procedure. Illustratively, one or more surgical grip points 220 may be configured to interface with a surgeon's fingertips. In one or more embodiments, one or more surgical grip points 220 may be configured to increase a total contact area between a surgeon's fingertips and handle 110. Illustratively, one or more surgical grip points 220 may be configured to facilitate an application of a compressive force to handle 110, e.g., by increasing a coefficient of friction between a surgeon's fingertips and handle 110 as the surgeon applies a compressive force to handle 110. Handle 110 may be manufactured from any suitable material, e.g., polymers, metals, metal alloys, etc., or from any combination of suitable materials.

In one or more embodiments, handle 110 may comprise one or more handle link pin housings 230. Illustratively, handle link pin housing 230 may be configured to house link pin 109. In one or more embodiments, nosecone 105 may comprise one or more nosecone link pin housings 235. Illustratively, nosecone link pin housing 235 may be configured to house link pin 109. In one or more embodiments, at least one link pin 109 may be configured to connect nosecone 105 to link 108, e.g., link pin 109 may be discs posed within both nosecone link pin housing 235 and link 108. Illustratively, at least one link pin 109 may be configured to connect handle 110 and link 108, e.g., link pin 109 may be disposed within both handle link pin housing 230 and link 108. In one or more embodiments, at least one link 108 may be connected to both nosecone 105 and handle 110, e.g., at least one link pin 109 may be disposed within both nosecone link pin housing 235 and link 108 and at least one link pin 109 may be disposed within both handle link pin housing 230 and link 108.

FIG. 2B illustrates a cross-sectional view of an assembled multi-utility surgical instrument 200. In one or more embodiments, nosecone 105 may comprise a nosecone inner bore 205. Illustratively, inner hypodermic tube distal end 141 may be fixed within nosecone inner bore 205, e.g., by a machine press fit, a biocompatible adhesive, etc. In one or more embodiments, outer nosecone proximal end 172 may be fixed within nosecone inner bore 205, e.g., by a machine press fit, a biocompatible adhesive, etc.

Illustratively, end plug 160 may comprise a surgical blank housing 240, an end plug inner bore 250, an interface taper 260, and a fixation mechanism housing 270. In one or more embodiments, end plug inner bore 250 may comprise an end plug inner bore distal cone 251 and an end plug inner bore proximal chamber 252. Illustratively, interface taper 260 may be configured to interface with one or more components, e.g., to provide one or more surgical utilities. In one or more embodiments, interface taper 260 may comprise a Luer taper. End plug 160 may be manufactured from any suitable material, e.g., polymers, metals, metal alloys, etc., or from any combination of suitable materials.

Illustratively, surgical blank 180 may be disposed within outer hypodermic tube 170, nosecone inner bore 205, inner hypodermic tube 140, piston tube 150, actuation facilitating sleeve 130, surgical blank housing 240, and fixation mechanism housing 270. In one or more embodiments, fixation mechanism 165 may be configured to fix surgical blank 180 in a position relative to handle 110, e.g., at fixation mechanism housing 270. For example, fixation mechanism 165 may be disposed within fixation mechanism housing 270, e.g., to fix surgical blank 180 in a position relative to handle 110.

Illustratively, surgical blank 180 may modified to provide a one or more surgical utilities, e.g., surgical blank distal end 181 may be modified to provide one or more particular surgical utilities of a plurality of surgical utilities. In one or more embodiments, surgical blank 180 may be modified wherein surgical blank 180 may comprise a surgical forceps, e.g., with a grasping utility. Illustratively, surgical blank 180 may be modified wherein surgical blank 180 may comprise a surgical scissors, e.g., with a cutting utility. In one or more embodiments, surgical blank 180 may be modified wherein surgical blank 180 may comprise a surgical manipulator, e.g., with a manipulation utility. Illustratively, surgical blank 180 may be modified wherein surgical blank 180 may comprise a surgical hook, e.g., with a hook utility. In one or more embodiments, surgical blank 180 may be modified wherein surgical blank 180 may comprise a surgical chopper, e.g. with a chopping utility. Illustratively, surgical blank 180 may be modified wherein surgical blank 180 may comprise a surgical pre-chopper, e.g., with a pre-chopping utility. In one or more embodiments, surgical blank 180 may be modified wherein surgical blank 180 may comprise a surgical pick, e.g., with a pick utility. Illustratively, surgical blank 180 may be modified to comprise any surgical instrument with any surgical utility as will be appreciated by one having ordinary skill in the relevant technological art. Surgical blank 180 may be manufactured from any suitable material, e.g., polymers, metals, metal alloys, etc., or from any combination of suitable materials.

In one or more embodiments, handle 110 may be compressed, e.g., by an application of a compressive force to handle 110. For example, a surgeon may compress handle 110 by gently squeezing handle 110, e.g., at one or more surgical grip points 220. Illustratively, a compression of handle 110 may be configured to actuate nosecone 105 relative to handle proximal end 112. Illustratively, a compression of handle 110 may be configured to extend nosecone 105 relative to handle proximal end 112.

In one or more embodiments, a compression of handle 110 may be configured to extend one or more links 108 connected to nosecone 105, e.g., by one or more link pins 109, away from handle proximal end 112. Illustratively, a compression of handle 110 may be configured to gradually project nosecone 105 relative to handle proximal end 112. In one or more embodiments, a compression of handle 110 may be configured to gradually actuate outer hypodermic tube 170 relative to handle proximal end 112. For example, a compression of handle 110 may be configured to gradually extend outer hypodermic tube 170 relative to handle proximal end 112. Illustratively, a compression of handle 110 may be configured to gradually actuate outer hypodermic tube 170 relative to surgical blank 180. For example, a compression of handle 110 may be configured to gradually extend outer hypodermic tube 170 relative to surgical blank 180.

In one or more embodiments, a compression of handle 110 may be configured to actuate inner hypodermic tube 140 relative to handle 110. Illustratively, a compression of handle 110 may be configured to extend inner hypodermic tube 140 relative to handle proximal end 112. In one or more embodiments, a compression of handle 110 may be configured to actuate piston tube 150 relative to handle 110. Illustratively, a compression of handle 110 may be configured to extend piston tube 150 relative to handle proximal end 112.

In one or more embodiments, handle 110 may be decompressed, e.g., by reducing a magnitude of a compressive force applied to handle 110. For example, a surgeon may decompress handle 110 by decreasing an amount of compressive force applied to handle 110, e.g., at one or more surgical grip points 220. Illustratively, a decompression of handle 110 may be configured to actuate nosecone 105 relative to handle proximal end 112. Illustratively, a decompression of handle 110 may be configured to retract nosecone 105 relative to handle proximal end 112.

In one or more embodiments, a decompression of handle 110 may be configured to retract one or more links 108 connected to nosecone 105, e.g., by one or more link pins 109, towards handle proximal end 112. Illustratively, a decompression of handle 110 may be configured to gradually retract nosecone 105 relative to handle proximal end 112. In one or more embodiments, a decompression of handle 110 may be configured to gradually actuate outer hypodermic tube 170 relative to handle proximal end 112. For example, a decompression of handle 110 may be configured to gradually retract outer hypodermic tube 170 relative to handle proximal end 112. Illustratively, a decompression of handle 110 may be configured to gradually actuate outer hypodermic tube 170 relative to surgical blank 180. For example, a decompression of handle 110 may be configured to gradually retract outer hypodermic tube 170 relative to surgical blank 180.

In one or more embodiments, a decompression of handle 110 may be configured to actuate inner hypodermic tube 140 relative to handle 110. Illustratively, a decompression of handle 110 may be configured to retract inner hypodermic tube 140 relative to handle proximal end 112. In one or more embodiments, a decompression of handle 110 may be configured to actuate piston tube 150 relative to handle 110. Illustratively, a decompression of handle 110 may be configured to retract piston tube 150 relative to handle proximal end 112.

In one or more embodiments, actuation facilitating sleeve 130 and piston tube 150 may be configured to minimize a coefficient of friction between actuation facilitating sleeve 130 and piston tube 150. Illustratively, actuation facilitating sleeve 130 and piston tube 150 may be manufactured from one or more materials configured to minimize a friction force, e.g., when piston tube 150 is actuated relative to handle 110. For example, actuation facilitation sleeve 130 and piston tube 150 may be manufactured from one or more materials configured to minimize a friction force, e.g., when piston tube 150 is actuated relative to actuation facilitating sleeve 130. In one or more embodiments, at least an inner portion of actuation facilitating sleeve 130 may comprise a non-crystalline material, e.g., glass. Illustratively, at least an outer portion of piston tube 150 may comprise carbon or a carbon allotrope, e.g., graphite. In one or more embodiments, at least an inner portion of actuation facilitating sleeve 130 may comprise a carbon or a carbon allotrope, e.g., graphite. Illustratively, at least an outer portion of piston tube 150 may comprise a non-crystalline material, e.g., glass.

Actuation facilitating sleeve 130 may be manufactured from any suitable material, e.g., polymers, metals, metal alloys, etc., or from any combination of suitable materials. Piston tube 150 may be manufactured from any suitable material, e.g., polymers, metals, metal alloys, etc., or from any combination of suitable materials. In one or more embodiments, an inner portion of actuation facilitating sleeve 130 may be coated with a material configured to minimize a coefficient of friction between actuation facilitating sleeve 130 and piston tube 150, e.g., Teflon. Illustratively, an outer portion of piston tube 150 may be coated with a material configured to minimize a coefficient of friction between piston tube 150 and actuation facilitation sleeve 130, e.g., Teflon.

Figure 3A:
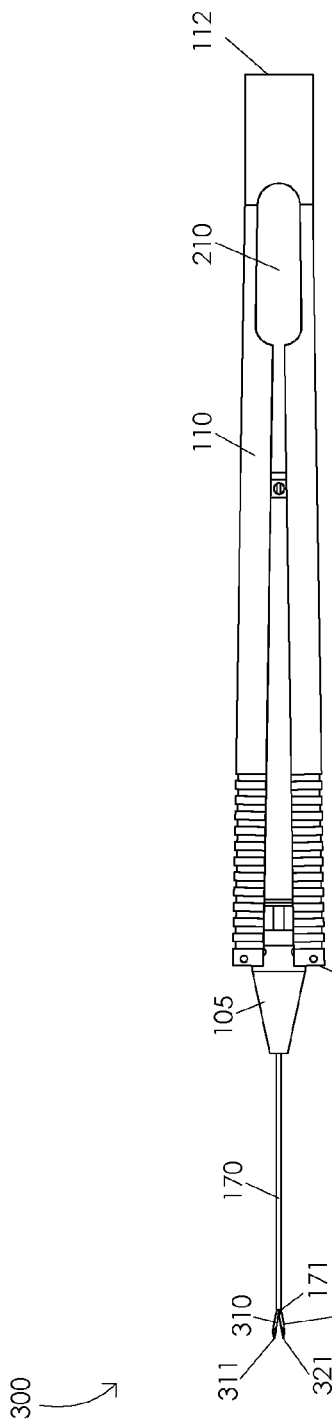
FIGS. 3A, 3B, and 3C are schematic diagrams illustrating a grasping utility of an assembled multi-utility surgical instrument.
Figure 3B:
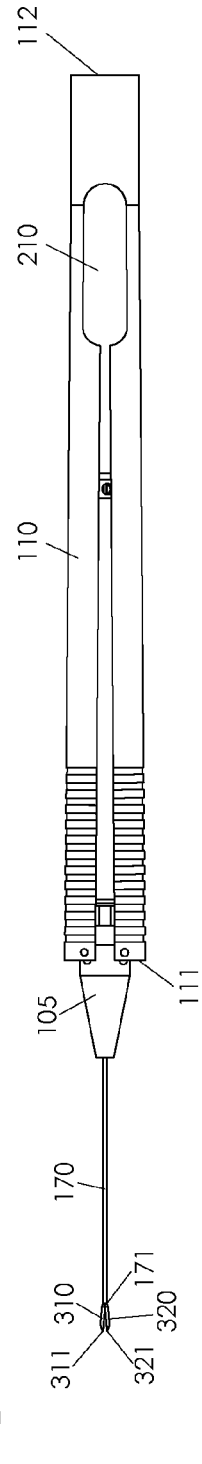
Figure 3C:
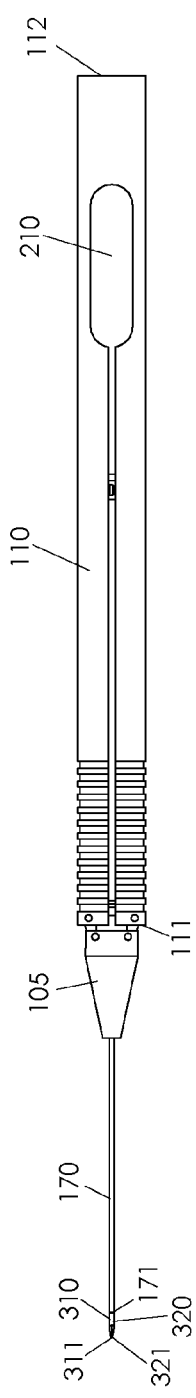

FIGS. 3A, 3B, and 3C are schematic diagrams illustrating a grasping utility of an assembled multi-utility surgical instrument 200. FIG. 3A illustrates an open forceps 300. In one or more embodiments, surgical blank 180 may be modified wherein surgical blank 180 may comprise an open forceps 300. For example, surgical blank distal end 180 may comprise a first forceps arm 310 and a second forceps arm 320. Illustratively, first forceps arm 310 may comprise a first forceps tip 311 and second forceps arm 320 may comprise a second forceps tip 321. In one or more embodiments, first forceps tip 311 and second forceps tip 321 may be separated at a first separated distance, e.g., when surgical blank 180 comprises an open forceps 300.

FIG. 3B illustrates a partially closed forceps 301. In one or more embodiments, a compression of handle 110, e.g., due to an application of a compressive force to handle 110, may be configured to gradually close an open forceps 300 wherein surgical blank 180 may comprise a partially closed forceps 301. Illustratively, a compression of handle 110 may be configured to gradually extend nosecone 105 and outer hypodermic tube 170 relative to surgical blank 180. Illustratively, as outer hypodermic tube 170 is gradually extended over surgical blank 180, outer hypodermic tube 170 may be configured to gradually reduce a separation distance between first forceps tip 311 and second forceps tip 321. For example, first forceps tip 311 and second forceps tip 321 may be separated at a second separated distance, e.g., when surgical blank 180 comprises a partially closed forceps 301. In one or more embodiments, the first separated distance may be greater than the second separated distance.

FIG. 3C illustrates a fully closed forceps 302. In one or more embodiments, a compression of handle 110 may be configured to gradually close a partially closed forceps 301 wherein surgical blank 180 may comprise a fully closed forceps 302. Illustratively, a compression of handle 110 may be configured to gradually extend outer hypodermic tube 170 over surgical blank 180. In one or more embodiments, as outer hypodermic tube 170 is gradually extended over surgical blank 180, outer hypodermic tube 170 may be configured to gradually reduce a separation distance between first forceps tip 311 and second forceps tip 321. If a separation distance between first forceps tip 311 and second forceps tip 321 is gradually reduced until first forceps tip 311 and second forceps tip 321 are separated by a minimal distance, e.g., first forceps tip 311 and second forceps tip 321 are in contact, then surgical blank 180 may comprise a fully closed forceps 302.

Figure 4A:
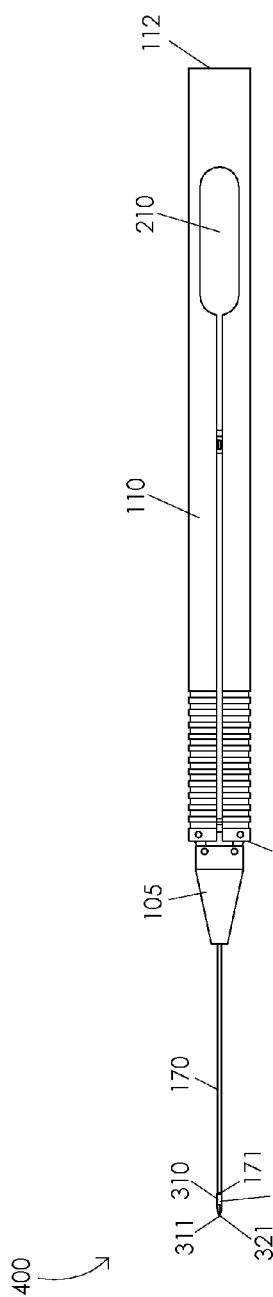
FIGS. 4A, 4B, and 4C are schematic diagrams illustrating a releasing utility of an assembled multi-utility surgical instrument.
Figure 4B:
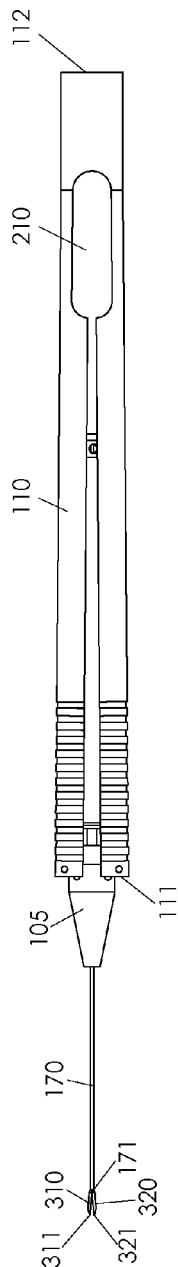
Figure 4C:
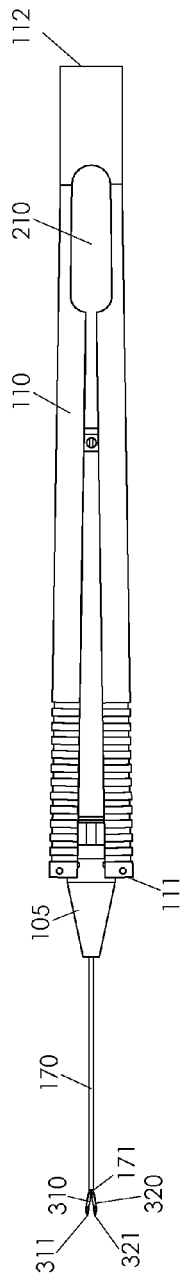

FIGS. 4A, 4B, and 4C are schematic diagrams illustrating a releasing utility of an assembled multi-utility surgical instrument 200. FIG. 4A illustrates a closed forceps 400. In one or more embodiments, surgical blank 180 may comprise a closed forceps 400, e.g., when first forceps tip 311 and second forceps tip 321 are separated by a minimal distance. Illustratively, a full compression of handle 110 may be configured to reduce a separation distance between first forceps tip 311 and second forceps tip 321 wherein surgical blank 180 may comprise a closed forceps 400.

FIG. 4B illustrates a partially open forceps 401. In one or more embodiments, surgical blank 180 may comprise a partially open forceps 401, e.g., when first forceps tip 311 and second forceps tip 321 are separated at a partially separated distance. Illustratively, a decompression of handle 110, e.g., due to a reduction of a magnitude of a compressive force applied to handle 110, may be configured to gradually retract nosecone 105 and outer hypodermic tube 170 relative to surgical blank 180. In one or more embodiments, as outer hypodermic tube 170 is gradually retracted relative to surgical blank 180, outer hypodermic tube 170 may be configured to gradually increase a separation distance between first forceps tip 311 and second forceps tip 321. Illustratively, a decompression of handle 110 may be configured to gradually open a closed forceps 400 wherein surgical blank 180 may comprise a partially open forceps 401.

FIG. 4C illustrates a fully open forceps 402. In one or more embodiments, surgical blank 180 may comprise a fully open forceps 402, e.g., when first forceps tip 311 and second forceps tip 321 are separated at a fully separated distance. Illustratively, the fully separated distance may be greater than the partially separated distance. In one or more embodiments, a decompression of handle 110 may be configured to gradually open a partially open forceps 401 wherein surgical blank 180 may comprise a fully open forceps 402. Illustratively, a decompression of handle 110 may be configured to gradually retract outer hypodermic tube 170 relative to surgical blank 180. In one or more embodiments, as outer hypodermic tube 170 is gradually retracted relative to surgical blank 180, outer hypodermic tube 170 may be configured to gradually increase a separation distance between first forceps tip 311 and second forceps tip 321. If a separation distance between first forceps tip 311 and second forceps tip 321 is gradually increased, e.g., by a full decompression of handle 110, until first forceps tip 311 and second forceps tip 321 are separated by a fully separated distance, then surgical blank 180 may comprise a fully open forceps 402.

Figure 5:
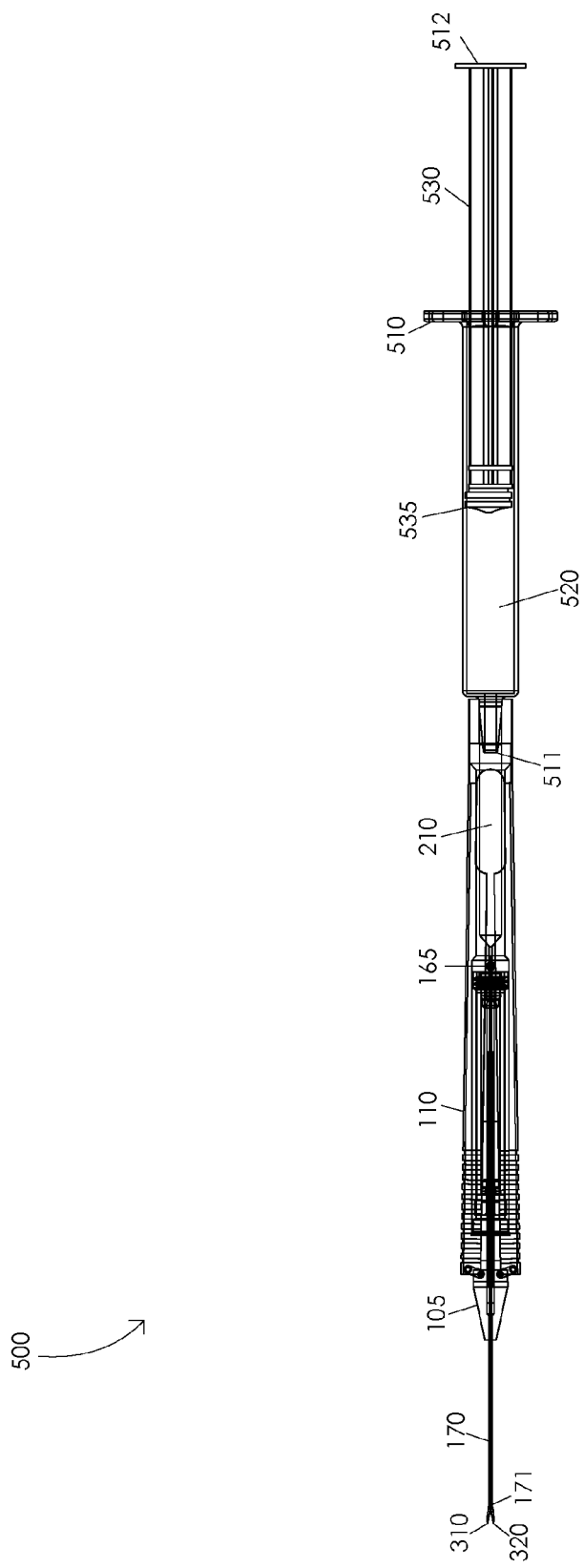
FIG. 5 is a schematic diagram illustrating a multi-utility surgical instrument flushing configuration.

FIG. 5 is a schematic diagram illustrating a multi-utility surgical instrument flushing configuration 500. In one or more embodiments, a multi-utility surgical instrument flushing configuration 500 may comprise an assembled multi-utility instrument 200 and a syringe 510 having a syringe distal end 511 and a syringe proximal end 512. Illustratively, syringe 510 may comprise a syringe chamber 520, a syringe pump 530, and a syringe plunger 535. In one or more embodiments, syringe 510 may be configured to interface with interface taper 260, e.g., to form a hermetic seal.

Illustratively, syringe chamber 520 may contain a fluid, e.g., water, saline, etc. In one or more embodiments, syringe pump 530 and syringe plunger 535 may be configured to flush a fluid contained in syringe chamber 520 through an inner portion of an assembled multi-utility surgical instrument 200, e.g., and expel the fluid from outer hypodermic tube distal end 271. Illustratively, a fluid may be flushed, e.g., by syringe pump 530 and syringe plunger 535, from syringe chamber 520 into end plug distal bore 250; from end plug distal bore 250 into surgical blank housing 240; from surgical blank housing 240 into piston tube 150; from piston tube 150 into inner hypodermic tube 140; from inner hypodermic tube 140 into nosecone inner bore 205; and from nosecone inner bore 205 into outer hypodermic tube 170. For example, after the fluid is flushed through outer hypodermic tube 170, the fluid may be expelled from outer hypodermic tube distal end 171.

In one or more embodiments, syringe pump 530 and syringe plunger 535 may be configured to remove undesirable material from first forceps arm 310 or second forceps arm 320. For example, when performing a surgical procedure, a forceps may be required to remove a delicate tissue or membrane. Illustratively, one or more pieces of a membrane may stick to first forceps arm 310 or second forceps arm 320 during a surgical procedure. In one or more embodiments, syringe pump 530 and syringe plunger 535 may be configured to remove undesirable material from first forceps arm 310 or second forceps arm 320, e.g., by flushing a fluid through an inner portion of assembled multi-utility surgical instrument 200 and washing the undesirable material off of first forceps arm 310 or second forceps arm 320 as the fluid is expelled from outer hypodermic tube distal end 171.

Illustratively, a multi-utility surgical instrument flushing configuration 500 may be configured to sterilize an assembled multi-utility surgical instrument 200. For example, flushing a fluid through an inner portion of an assembled multi-utility surgical instrument 200 may be configured to remove biological matter that may have accumulated within the inner portion of assembled multi-utility surgical instrument 200, e.g., from passive ingress. In one or more embodiments, an unsterilized assembled multi-utility surgical instrument 200 may be sterilized by flushing a fluid through an inner portion of the unsterilized assembled multi-utility surgical instrument 200 and then subjecting the unsterilized assembled multi-utility surgical instrument 200 to a high heat and high pressure environment, e.g., in an autoclave.

FIGS. 6A and 6B are schematic diagrams illustrating a multi-utility surgical instrument with an irrigation utility 600. FIG. 6A illustrates a side view of a multi-utility surgical instrument with an irrigation utility 600. In one or more embodiments, a multi-utility surgical instrument with an irrigation utility 600 may comprise an irrigation tube 610, an instrument interface 620 having an instrument interface distal end 621 and an instrument interface proximal end 622, an irrigation component interface 630 having an irrigation component interface distal end 631 and an irrigation component interface proximal end 632, and an irrigation component 640. Illustratively, instrument interface 620 may be configured to interface with interface taper 260, e.g., to form a hermetic seal. In one or more embodiments, irrigation component interface 630 may be configured to interface with irrigation component 640. Illustratively, irrigation component 640 may be configured to provide an irrigation fluid and control an irrigation fluid flow. In one or more embodiments, irrigation component 640 may comprise a phacoemulsification/vitrectomy machine or irrigation component 640 may be configured to interface with a phacoemulsification/vitrectomy machine. Illustratively, a first end of irrigation tube 610 may be connected to instrument interface 620, e.g., at instrument interface proximal end 622, and a second end of irrigation tube 610 may be connected to irrigation component interface 630, e.g., at irrigation component interface distal end 631. In one or more embodiments, irrigation tube 610 may be configured to guide an irrigation fluid flow, e.g., provided by irrigation component 640.

Illustratively, a portion of outer hypodermic tube 170 may be disposed below the surface of a particular tissue 650, e.g., outer hypodermic tube distal end 171 may be disposed below the surface of a particular tissue 650. In one or more embodiments, outer hypodermic tube 170 may be inserted through a small incision in particular tissue 650. Illustratively, particular tissue 650 may comprise a vitreous tissue.

FIG. 6B illustrates a cross-sectional view of multi-utility surgical instrument with an irrigation utility 600. In one or more embodiments, irrigation component 640 may be configured to initiate an irrigation procedure. For example, irrigation component 640 may initiate an irrigation procedure by pumping an irrigation fluid into irrigation tube 610. Illustratively, irrigation component 640 may be configured to control an irrigation fluid flow out of irrigation component 640. In one or more embodiments, irrigation component 640 may be configured to control an irrigation fluid flow from irrigation component 640 into irrigation tube 610; from irrigation tube 610 into end plug distal bore 250; from end plug distal bore 250 into surgical blank housing 240; from surgical blank housing 240 into piston tube 150; from piston tube 150 into inner hypodermic tube 140; from inner hypodermic tube 140 into nosecone inner bore 205; from nosecone inner bore 205 into outer hypodermic tube 170; and from outer hypodermic tube 170 into an irrigation target.

Illustratively, a multi-utility surgical instrument with an irrigation utility 600 may be configured to clear debris or fluid from a surgical site, e.g., to improve a visualization of the surgical site. For example, one or more features of a surgical site may become difficult for a surgeon to visualize due to the presence of blood or debris during a surgical procedure. In one or more embodiments, a multi-utility surgical instrument with an irrigation utility 600 may be configured to clear blood or debris from a surgical site by washing the blood or debris from the surgical site with an irrigation fluid. Illustratively, a multi-utility surgical instrument with an irrigation utility 600 may be configured to provide a clear visual field in close proximity to a bleeding vessel, e.g., by washing blood from the visual field with an irrigation fluid.

Figure 7A:
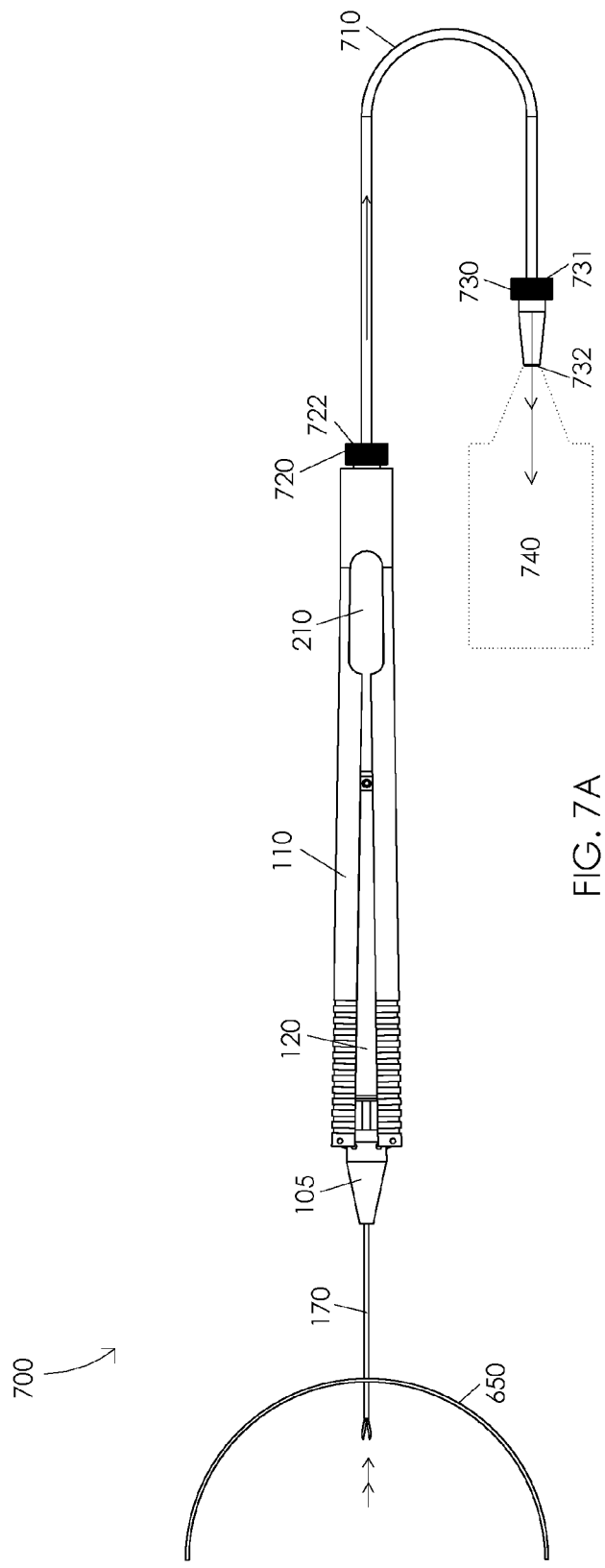
FIGS. 7A and 7B are schematic diagrams illustrating a multi-utility surgical instrument with an aspiration utility.
Figure 7B:
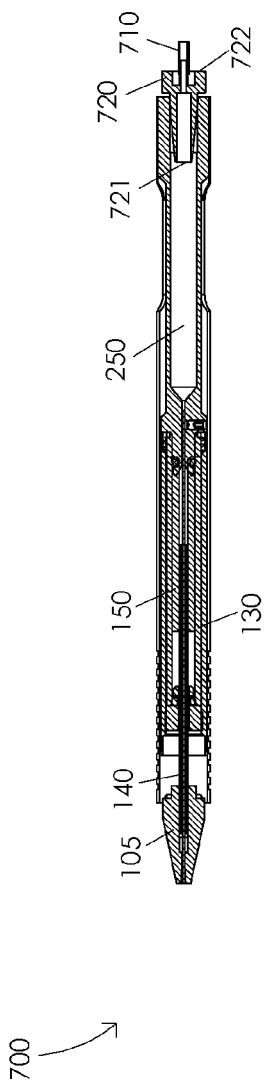

FIGS. 7A and 7B are schematic diagrams illustrating a multi-utility surgical instrument with an aspiration utility 700. FIG. 7A illustrates a side view of a multi-utility surgical instrument with an aspiration utility 700. In one or more embodiments, a multi-utility surgical instrument with an aspiration utility 700 may comprise an aspiration tube 710, an instrument interface 720 having an instrument interface distal end 721 and an instrument interface proximal end 722, an aspiration component interface 730 having an aspiration component interface distal end 731 and an aspiration component interface proximal end 732, and an aspiration component 740. Illustratively, instrument interface 720 may be configured to interface with interface taper 260, e.g., to form a hermetic seal. In one or more embodiments, aspiration component interface 730 may be configured to interface with aspiration component 740. Illustratively, aspiration component 740 may be configured to provide an aspiration vacuum. In one or more embodiments, aspiration component 740 may comprise a phacoemulsification/vitrectomy machine or aspiration component 740 may be configured to interface with a phacoemulsification/vitrectomy machine. Illustratively, a first end of aspiration tube 710 may be connected to instrument interface 720, e.g., at instrument interface proximal end 722, and a second end of aspiration tube 710 may be connected to aspiration component interface 730, e.g., at aspiration component interface distal end 731. In one or more embodiments, aspiration tube 710 may be configured to contain an aspiration vacuum, e.g., provided by aspiration component 740.

Illustratively, a portion of outer hypodermic tube 170 may be disposed below the surface of a particular tissue 650, e.g., outer hypodermic tube distal end 171 may be disposed below the surface of a particular tissue 650. In one or more embodiments, outer hypodermic tube 170 may be inserted through a small incision in particular tissue 650. Illustratively, particular tissue 650 may comprise a vitreous tissue.

FIG. 7B illustrates a cross-sectional view of multi-utility surgical instrument with an aspiration utility 700. In one or more embodiments, aspiration component 740 may be configured to initiate an aspiration procedure. For example, aspiration component 740 may initiate an aspiration procedure by inducing an aspiration vacuum in aspiration tube 710. Illustratively, an aspiration vacuum may be configured to aspirate an aspiration target into outer hypodermic tube 170; from outer hypodermic tube 170 into nosecone inner bore 205; from nosecone inner bore 205 into inner hypodermic tube 140; from inner hypodermic tube 140 into piston tube 150; from piston tube 150 into surgical blank housing 240; from surgical blank housing 240 into end plug inner bore 250; from end plug inner bore 250 into aspiration tube 710; and from aspiration tube 710 into aspiration component 740, e.g., for disposal.

Illustratively, a multi-utility surgical instrument with an aspiration utility 700 may be configured to clear debris or fluid from a surgical site, e.g., to improve a visualization of the surgical site. For example, one or more features of a surgical site may become difficult for a surgeon to visualize due to the presence of blood or debris during a surgical procedure. In one or more embodiments, a multi-utility surgical instrument with an aspiration utility 700 may be configured to clear blood or debris from a surgical site by removing the blood or debris from the surgical site with an aspiration vacuum. Illustratively, a multi-utility surgical instrument with an aspiration utility 700 may be configured to provide a clear visual field in close proximity to a bleeding vessel, e.g., by removing blood from the visual field with an aspiration vacuum.

FIGS. 8A, 8B, and 8C are schematic diagrams illustrating a multi-utility surgical instrument with an illumination utility 800. FIG. 8A illustrates a side view of a multi-utility surgical instrument with an illumination utility 800. In one or more embodiments, a multi-utility surgical instrument with an illumination utility 800 may comprise an assembled multi-utility surgical instrument 200, a light source interface 810, and an optic fiber 820 having an optic fiber distal end 821 and an optic fiber proximal end 822. Illustratively, optic fiber 820 may be configured to transmit light, e.g., between optic fiber proximal end 822 and optic fiber distal end 821. In one or more embodiments, optic fiber proximal end 822 may be disposed in light source interface 810. Illustratively, light source interface 810 may be configured to interface with a light source, e.g., an LED light source. In one or more embodiments, light source interface 810 may be configured to direct light, e.g., from a light source, towards optic fiber proximal end 822.

FIG. 8B illustrates a cross-sectional view of a multi-utility surgical instrument with an illumination utility 800. In one or more embodiments, optic fiber 820 may be disposed within an inner portion of an assembled multi-utility surgical instrument 200. Illustratively, optic fiber 820 may be disposed within end plug inner bore 250, surgical blank housing 240, piston tube 150, inner hypodermic tube 140, nosecone inner bore 205, and outer hypodermic tube 170. FIG. 8C illustrates an enlarged view of an outer hypodermic tube distal end 171 of a multi-utility surgical instrument with an illumination utility 800. In one or more embodiments, optic fiber 820 may be disposed within an inner portion of an assembled multi-utility surgical instrument 200 wherein optic fiber distal end 821 may be adjacent to outer hypodermic tube distal end 171.

Illustratively, a portion of outer hypodermic tube 170 may be disposed below the surface of a particular tissue 650, e.g., outer hypodermic tube distal end 171 may be disposed below the surface of a particular tissue 650. In one or more embodiments, outer hypodermic tube 170 may be inserted through a small incision in particular tissue 650. Illustratively, particular tissue 650 may comprise a vitreous tissue. In one or more embodiments, light source interface 810 may be configured to direct light, e.g., from a light source, towards optic fiber proximal end 822. Illustratively, optic fiber 820 may be configured to transmit light from optic fiber proximal end 822, e.g., through an inner portion of an assembled multi-utility surgical instrument 200, to optic fiber distal end 821. In one or more embodiments, optic fiber distal end 821 may be configured to direct light, e.g., from a light source, towards one or more illumination targets.

FIGS. 9A and 9B are schematic diagrams illustrating a multi-utility surgical instrument with a drug delivery utility 900. FIG. 9A illustrates a side view of a multi-utility surgical instrument with a drug delivery utility 900. In one or more embodiments, a multi-utility surgical instrument with a drug delivery utility 900 may comprise a drug delivery tube 910, an instrument interface 920 having an instrument interface distal end 921 and an instrument interface proximal end 922, a drug delivery component interface 930 having a drug delivery component interface distal end 931 and a drug delivery component interface proximal end 932, and a drug delivery component 940. Illustratively, instrument interface 920 may be configured to interface with interface taper 260, e.g., to form a hermetic seal. In one or more embodiments, drug delivery component interface 930 may be configured to interface with drug delivery component 940.

Illustratively, drug delivery component 940 may be configured to provide a drug infusion and control a drug infusion flow. In one or more embodiments, drug delivery component 940 may comprise an infusion pump. Illustratively, a first end of drug delivery tube 910 may be connected to instrument interface 920, e.g., at instrument interface proximal end 922, and a second end of drug delivery tube 910 may be connected to drug delivery component interface 930, e.g., at drug delivery component interface distal end 931. In one or more embodiments, drug delivery tube 910 may be configured to guide a drug infusion flow, e.g., provided by drug delivery component 940.

Illustratively, a portion of outer hypodermic tube 170 may be disposed below the surface of a particular tissue 650, e.g., outer hypodermic tube distal end 171 may be disposed below the surface of a particular tissue 650. In one or more embodiments, outer hypodermic tube 170 may be inserted through a small incision in particular tissue 650. Illustratively, particular tissue 650 may comprise a vitreous tissue.

FIG. 9B illustrates a cross-sectional view of multi-utility surgical instrument with a drug delivery utility 900. In one or more embodiments, drug delivery component 940 may be configured to initiate a drug delivery procedure. For example, drug delivery component 940 may initiate a drug delivery procedure by infusing a drug into drug delivery tube 910. Illustratively, drug delivery component 940 may be configured to control a drug infusion flow out of drug delivery component 940. In one or more embodiments, drug delivery component 940 may be configured to control a drug infusion flow from drug delivery component 940 into drug delivery tube 910; from drug delivery tube 910 into end plug distal bore 250; from end plug distal bore 250 into surgical blank housing 240; from surgical blank housing 240 into piston tube 150; from piston tube 150 into inner hypodermic tube 140; from inner hypodermic tube 140 into nosecone inner bore 205; from nosecone inner bore 205 into outer hypodermic tube 170; and from outer hypodermic tube 170 into a drug delivery target.

Illustratively, a multi-utility surgical instrument with a drug delivery utility 900 may be configured to administer antibiotics or steroids to a particular surgical area as a surgeon performs a surgical procedure at the particular surgical area. For example, a particular surgical procedure may require a surgeon to first locate a membrane at a surgical site and then remove the membrane from the surgical site. In one or more embodiments, a surgeon may use a multi-utility surgical instrument with a drug delivery utility 900 to locate the membrane at the surgical site by administering a drug, e.g., a steroid, to the surgical site for visualization of the membrane. Illustratively, after locating the membrane at the surgical site, the surgeon may remove the membrane from the surgical site, e.g., with a grasping utility of an assembled multi-utility surgical instrument 200. In one or more embodiments, a multi-utility surgical instrument flushing configuration 500 may be configured to remove any portions of the membrane from an assembled multi-utility surgical instrument 200, e.g., to sterilize the assembled multi-utility surgical instrument 200.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any instrument. Furthermore, while this description has been written in terms of a multi-utility surgical instrument, the teachings of the present invention are equally suitable to systems where the functionality of one or more utilities may be employed. Therefore, it is the object of the appended claims to cover all such variations and modifications as come within the true spirit and scope of the invention.

What is claimed is:

1. An instrument comprising:
   a handle having a handle distal end and a handle proximal end;
   a housing sleeve disposed within the handle;
   an actuation facilitating sleeve disposed within the housing sleeve;
   a piston tube disposed within the actuation facilitating sleeve;
   an end plug disposed within the handle, the end plug having an end plug inner bore and an interface taper configured to interface with a syringe;
   a nosecone attached to the handle distal end, the nosecone having a nosecone inner bore;
   an inner hypodermic tube fixed to the nosecone, the inner hypodermic tube at least partially disposed within the piston tube; and
   an outer hypodermic tube having an outer hypodermic tube distal end and an outer hypodermic tube proximal end wherein the outer hypodermic tube proximal end is fixed to the nosecone.

2. The instrument of claim 1 further comprising:
   a surgical blank disposed within the outer hypodermic tube, the nosecone inner bore, the inner hypodermic tube, the piston tube, and a surgical blank housing of the end plug.

3. The instrument of claim 2 wherein the syringe is configured to flush a fluid into the end plug inner bore and expel the fluid out from the outer hypodermic tube distal end.

4. The instrument of claim 3 wherein the syringe is configured to remove biological matter from an inner portion of the instrument.

5. The instrument of claim 3 wherein the syringe is configured to remove biological matter from a distal end of the surgical blank.

6. The instrument of claim 5 wherein the distal end of the surgical blank comprises a forceps.

7. The instrument of claim 5 wherein the distal end of the surgical blank comprises a scissors.

8. The instrument of claim 1 wherein at least a portion of the actuation facilitating sleeve comprises graphite.

9. The instrument of claim 1 wherein at least a portion of the actuation facilitating sleeve comprises glass.

10. The instrument of claim 1 wherein at least a portion of the piston tube comprises graphite.

11. The instrument of claim 1 wherein at least a portion of the piston tube comprises glass.

12. The instrument of claim 2 wherein a compression of the handle is configured to extend the nosecone relative to the handle proximal end.

13. The instrument of claim 12 wherein the compression of the handle is configured to extend the outer hypodermic tube relative to the surgical blank.

14. The instrument of claim 2 wherein a decompression of the handle is configured to retract the nosecone relative to the handle proximal end.

15. The instrument of claim 14 wherein the decompression of the handle is configured to retract the outer hypodermic tube relative to the surgical blank.

16. The instrument of claim 1 wherein the interface taper comprises a Luer taper.

17. The instrument of claim 1 further comprising:
   a proximal O-ring disposed over a portion of the end plug.

18. The instrument of claim 17 wherein the proximal O-ring is disposed in the housing sleeve and the actuation facilitating sleeve.

19. The instrument of claim 1 further comprising:
   a front plug; and
   a distal O-ring, the distal O-ring disposed over a portion of the front plug.

20. The instrument of claim 19 wherein the distal O-ring is disposed in the housing sleeve and the actuation facilitating sleeve.

\* \* \* \* \*